(12) United States Patent
Foes et al.

(10) Patent No.: US 7,591,583 B2
(45) Date of Patent: Sep. 22, 2009

(54) TRANSIENT DEFECT DETECTION ALGORITHM

(75) Inventors: Scott Foes, Ann Arbor, MI (US); Hamid Yazdi, Ann Arbor, MI (US)

(73) Assignee: Federal-Mogul World Wide, Inc., Southfield, MI (US)

( * ) Notice: Subject to any disclaimer, the term of this patent is extended or adjusted under 35 U.S.C. 154(b) by 5 days.

(21) Appl. No.: 11/131,628

(22) Filed: May 18, 2005

(65) Prior Publication Data
US 2006/0262971 A1 Nov. 23, 2006

(51) Int. Cl.
*G01N 25/72* (2006.01)
(52) U.S. Cl. .......................... 374/5; 374/124; 374/120; 374/137; 374/45; 250/338.1
(58) Field of Classification Search ......... 374/120–121, 374/4–5, 45, 44, 57, 124, 129, 141, 137; 250/338.1, 338.3, 339.04, 339.02, 339.06, 250/341.1; 252/964, 962; 702/33, 34, 35, 702/40; 73/592, 964, 962
See application file for complete search history.

(56) References Cited

U.S. PATENT DOCUMENTS

| | | | | |
|---|---|---|---|---|
| 4,811,090 A | * | 3/1989 | Khurana | 348/79 |
| 4,999,500 A | * | 3/1991 | Breskin et al. | 250/385.1 |
| 5,095,204 A | | 3/1992 | Novini | |
| 5,157,451 A | * | 10/1992 | Taboada et al. | 356/5.05 |
| 5,172,005 A | | 12/1992 | Cochran et al. | |
| 5,287,183 A | * | 2/1994 | Thomas et al. | 348/571 |
| 5,294,198 A | * | 3/1994 | Schlagheck | 374/4 |
| 5,582,485 A | * | 12/1996 | Lesniak | 374/5 |
| 5,631,465 A | | 5/1997 | Shepard | |
| 5,654,977 A | * | 8/1997 | Morris | 374/4 |
| 5,711,603 A | * | 1/1998 | Ringermacher et al. | 374/5 |
| 6,033,107 A | | 3/2000 | Farina et al. | |
| 6,367,969 B1 | | 4/2002 | Ringermacher et al. | |
| 6,373,557 B1 | * | 4/2002 | Mengel et al. | 356/4.07 |
| 6,394,646 B1 | | 5/2002 | Ringermacher et al. | |
| 6,461,035 B2 | | 10/2002 | Meinlschmidt et al. | |
| 6,516,084 B2 | | 2/2003 | Shepard | |
| 6,517,236 B2 | | 2/2003 | Sun et al. | |
| 6,542,849 B2 | * | 4/2003 | Sun | 702/172 |
| 6,712,502 B2 | | 3/2004 | Zalameda et al. | |

(Continued)

*Primary Examiner*—Gail Verbitsky
(74) *Attorney, Agent, or Firm*—Robert L. Stearns; Dickinson Wright PLLC

(57) ABSTRACT

The invention provides an apparatus and method for detecting flaws in an object. The method includes the step of heating a portion of a surface of an object wherein the surface is defined by a plurality of individual surface elements. The method also includes the step of recording a plurality of thermal images of the portion over time with a thermal imaging device. Each of the plurality of thermal images is defined by a plurality of pixels. Each of the plurality of pixels has an individual pixel address and corresponds to one of the plurality of individual surface elements. The method also includes the step of determining a pixel intensity for each of the plurality pixels in each of the plurality of thermal images. The method also includes the step of integrating the pixel intensity of each of the plurality of pixels having the same individual address from respective thermal images to establish elements within an array of integrated pixel intensity. The method also includes the step of using the array of integrated pixel intensity to detect a flaw in the object.

6 Claims, 5 Drawing Sheets

U.S. PATENT DOCUMENTS

| | | | |
|---|---|---|---|
| 6,751,342 B2 * | 6/2004 | Shepard .................... | 382/141 |
| 6,759,659 B2 * | 7/2004 | Thomas et al. ........... | 250/341.6 |
| 6,874,932 B2 * | 4/2005 | Devitt et al. .................. | 374/5 |
| 6,963,369 B1 * | 11/2005 | Olding ...................... | 348/241 |
| 6,987,536 B2 * | 1/2006 | Olding et al. ............... | 348/297 |
| 7,009,695 B2 * | 3/2006 | Some ...................... | 356/237.1 |
| 7,016,372 B2 * | 3/2006 | Haartsen ................... | 348/308 |
| 7,018,094 B1 * | 3/2006 | Bates ........................ | 374/121 |
| 7,034,300 B2 * | 4/2006 | Hamrelius et al. .......... | 250/332 |
| 7,083,327 B1 * | 8/2006 | Shepard ...................... | 374/46 |
| 2002/0140842 A1 * | 10/2002 | Olding et al. ............... | 348/362 |
| 2004/0051782 A1 * | 3/2004 | Bradski ..................... | 348/36 |
| 2004/0076316 A1 * | 4/2004 | Fauci ......................... | 382/128 |
| 2005/0002546 A1 * | 1/2005 | Florent et al. ............... | 382/128 |
| 2005/0057670 A1 * | 3/2005 | Tull et al. ................... | 348/241 |
| 2005/0147150 A1 * | 7/2005 | Wickersham et al. ....... | 374/120 |
| 2006/0008170 A1 * | 1/2006 | Beausoleil et al. .......... | 382/254 |
| 2007/0158636 A1 * | 7/2007 | Tezuka ....................... | 257/10 |
| 2007/0160308 A1 * | 7/2007 | Jones et al. ................. | 382/260 |

* cited by examiner

TRANSIENT DEFECT DETECTION ALGORITHM

BACKGROUND OF THE INVENTION

1. Technical Field

The present invention relates generally to a nondestructive testing apparatus and method of nondestructive testing. More particularly, it relates to an apparatus and method for nondestructive testing of an object surface to determine the location of surface and subsurface flaws or other features using transient infrared thermography.

2. Related Art

The presence and location of both surface and subsurface flaws can be determined by various methods or techniques, including through the use of transient thermography. Transient thermography techniques generally utilize variations in the transfer of heat through an object over time to identify surface and subsurface flaws.

One transient thermographic method records the temperature rise of each resolution element by capturing a series of image arrays using an infrared camera while heating the surface of an object to be tested, and analyzing the temperature rise as a function of time to identify whether a linear temperature increase versus the square root of the heating time, occurs. Such behavior is reported to be indicative of the existence of a flaw within the object. This method is also reported to be of limited applicability for testing objects with complex geometries, or those which are otherwise subject to non-uniform heating transfer through the object.

One method of transient thermography comprises heating the surface of an object and analyzing individual infrared images of the object surface as a function of time. Flaws, particularly subsurface flaws, may be identified in the images by "hot spots" or regions of higher intensity infrared radiation because the rate at which heat transfers through the flaws is less than the rate at which it transfers in regions which do not include flaws. One limitation associated with this method is that the transient thermographic analysis is reduced to analyzing individual images which each represent a single point of time. This technique is of limited applicability with operators because of the possibility of missing a flaw indication because it requires analysis of multiple images which may have only minor variations to identify a flaw. Further, it is not easily adaptable to automation.

Another reported thermographic NDT technique utilizes a video replay of the recorded images and visual identification of intensity variations or bright spots by an operator to detect flaws. This technique is also not readily automatable. Further, it is highly operator dependent, and defects may easily be missed if the operator's attention is drawn away while observing the video. This technique also generally does not provide quantitative information about the location and or depth of the flaw.

A method of transient depth thermography is described in U.S. Pat. No. 5,711,603 to Ringermacher et al. This method involves heating the surface of the object and recording successive thermal images of each resolution element or pixel of the surface over a period of time. The contrast of each pixel is determined for each successive thermal image of the surface by determining the mean pixel intensity for that thermal image and subtracting the mean pixel intensity from the individual pixel intensity. The location of a flaw within the object is based upon changes in the pixel contrast.

SUMMARY OF THE INVENTION

The invention provides an apparatus and method for detecting flaws in an object. The method includes the step of heating a portion of a surface of an object wherein the surface is defined by a plurality of individual surface elements. The method also includes the step of recording a plurality of thermal images of the portion over time with a thermal imaging device. Each of the plurality of thermal images is defined by a plurality of pixels. Each of the plurality of pixels has an individual pixel address and corresponds to one of the plurality of individual surface elements. The method also includes the step of determining a pixel intensity for each of the plurality pixels in each of the plurality of thermal images. The method also includes the step of integrating the pixel intensity of each of the plurality of pixels having the same individual address from respective thermal images to establish elements within an array of integrated pixel intensity. The method also includes the step of using the array of integrated pixel intensity to detect a flaw in the object.

BRIEF DESCRIPTION OF THE DRAWINGS

These and other features and advantages of the present invention will become more readily appreciated when considered in connection with the following detailed description and appended drawings, wherein.

DETAILED DESCRIPTION OF THE PREFERRED EMBODIMENT

The exemplary embodiment of the present invention is an automated and nondestructive testing method and apparatus for performing transient thermographic analysis to determine the presence or absence of flaws, including both surface and subsurface flaws, in an object. The method may also be used to determine and/or generate an image of a flaw and its location in relation to the object surface. The method integrates temperature related data about the object in the form of integrated pixel intensity or amplitude from a series of thermal images of the object surface, each of which comprise an array of pixels, taken over a period of time or as a function of time. The integrated intensity of each of the various pixel locations which make up the thermal images can be analyzed to identify variations which are indicative of defects.

In the context of the present invention, a pixel is the smallest unit or picture element of a thermal image. Pixels are generally rectangular in shape, but may comprise other shapes also. A thermal image is made up of a two dimensional array of pixels, with the number of pixels determining the size of the image. A surface element is an area of the surface of the object being imaged, which is generally rectangular, and which corresponds to and is represented by a single pixel. The array of pixels, therefore, corresponds to an array of surface elements, such that a thermal image comprising an array of pixels corresponds to an array of surface elements which in turn corresponds to a composite area of the surface of the object. The size of the composite area of the surface is related to the magnification factor associated with the thermal imaging device used to make the thermal image.

Figure 1:
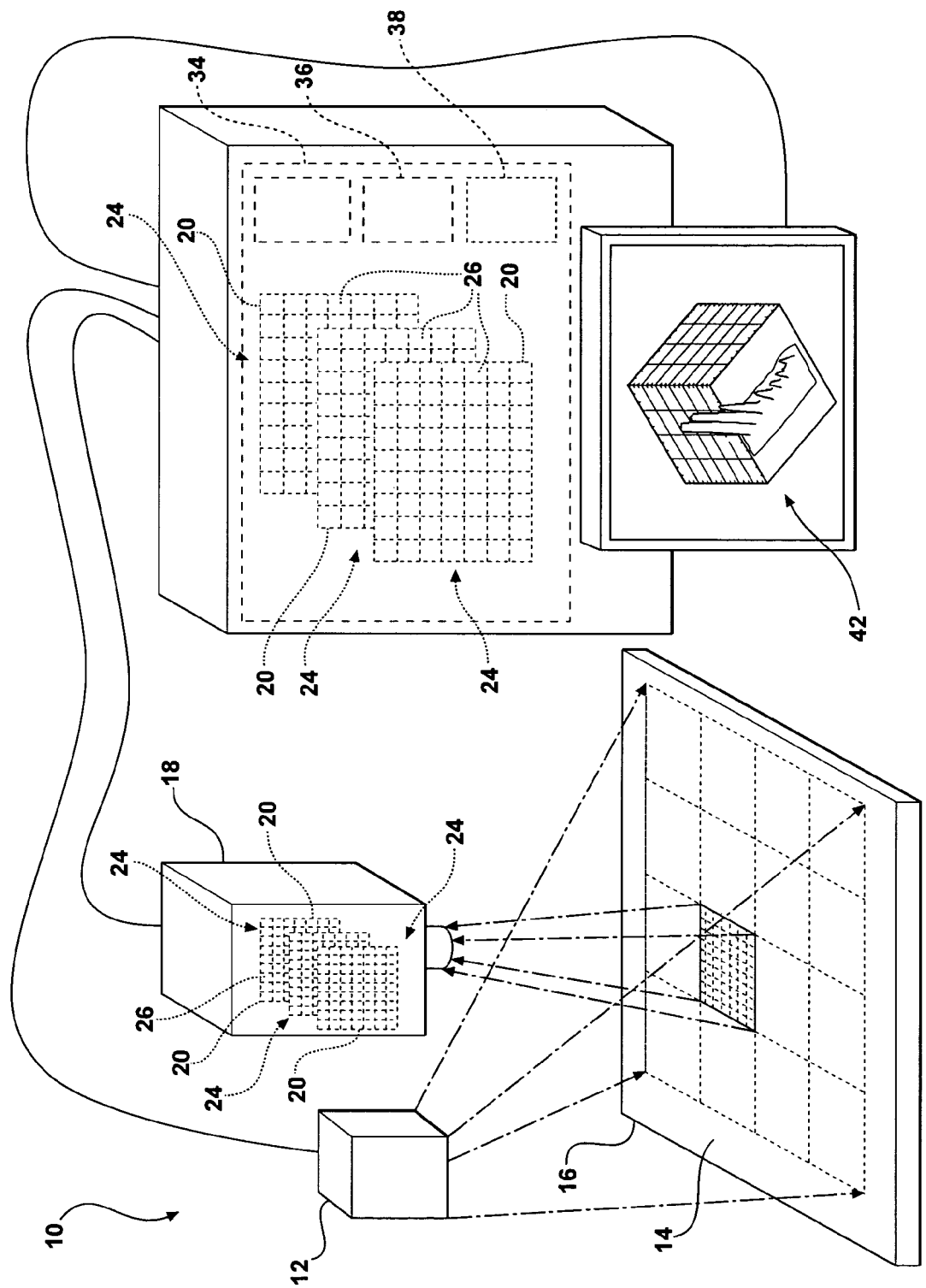
FIG. 1 is a schematic representation of the apparatus of the invention.

Referring to FIG. 1, in an exemplary embodiment of the invention, an apparatus 10 is operable to detect flaws in an object having a surface. Apparatus 10 is adapted to perform a form of transient thermographic analysis to determine the presence or absence of flaws, including both a surface and subsurface flaws, in an object. Apparatus 10 includes a heater 12 for heating a surface 14 of an object 16. Apparatus 10 also includes a thermal imaging device 18 which is adapted to produce a series of thermal images 20 of the surface 14 as a function of time and provide the thermal images 20 as a signal output. Each of the thermal images 20 is made up of an array 24 of pixels 26. Each pixel 26 has a unique pixel address in the array 24 and corresponds to a surface element in an array of surface elements that makes up a portion of the surface 14 of object 16. Apparatus 10 also includes a recorder 34 that is in signal communication with the thermal imaging device 18. Recorder 34 is adapted to capture the thermal images 20 for subsequent analysis. Apparatus 10 also includes means 36 for determining a pixel intensity for each of the pixels 26 in each of the thermal images. Apparatus 10 also includes means 38 for integrating the pixel intensity of the pixels 26 having the same address from each of the plurality of thermal images 20 for each pixel address. Means 38 is also operable to establish an array 42 of integrated pixel intensity.

The apparatus 10 may be used to detect surface and subsurface flaws in objects formed from most solid materials, including those made from metals, ceramics, glasses, engineering plastics, elastomers, composites and the like, and combinations thereof. The depth to which defects may be detected will depend upon the materials, the size of the defect and the particular elements of the apparatus and their design, features and capabilities. While applicant has observed the ability to detect defects in metal sheets of up to about 0.004 inches below the surface, and in rubber somewhat deeper, it is believed that defects located substantially deeper can be detected by appropriate design and selection of the elements of apparatus 10 and details of the method of its operation. For example, the amount of energy that reaches the defect area can be increased. One challenge in detecting defects in metal is the difficulty of getting energy into the test specimen. When the flash technique is used the heat the part, a portion of the energy is reflected off of the surface of the part. Heating techniques that are able to get more energy to the defect region will provide greater contrast. Alternatively, the surface finish of the part being inspected can be altered by changing the surface finish of the part being inspected. The surface of the part being inspected can be painted to change the surface finish. Alternatively, the parameters of the program can be changed to enhance defect identification. The following parameters can be changed to enhance defect contrast in some operating environments: the number of images considered, the frame rate, adjusting the numerical integration technique, adjusting the delay between flash and first image.

The heater 12 of the exemplary embodiment of the invention may include a photographic flash lamp, quartz lamp, infrared lamp, laser or other like device for delivering thermal energy to the surface 14 of object 16. In a preferred embodiment, a plurality of photographic flash lamps was utilized as heater 12 and was adapted to deliver about 4800 watt-sec of energy to the surface 14 of object 16. Heater 12 should be capable of heating the surface to a sufficient temperature to allow thermographic monitoring in accordance with the method described herein.

Many types of infrared cameras may be employed as the thermal imaging device 18. The thermal imaging device 18 of the exemplary embodiment of the invention is preferably an infrared camera with a focal plane array infrared detector. The video device is preferably a high speed focal plane array camera, or similar device, with a variable frame rate. The variable frame rate range may vary from, for example from about 50 frames per second up to about 250 frames per second or greater.

One example of an infrared camera that may be used in conjunction with the apparatus and method of the invention is the ThermaCAM SC 3000 Quantum Well Infrared Photodetector (QWIP) System made by FLIR Systems, Inc. This camera provides infrared imaging in the 8 to 9 um wavelength IR band by utilizing a Quantum Well Infrared Photodetector focal plane array IR detector having a sensitivity of less than 20 mK at 30° C. A wide range of lenses and other optics may be utilized to obtain the desired viewing area of the object for objects of varying size located at various distances from the camera.

The camera is adapted to provide analysis of dynamic or digitally stored images, and is adapted to provide image output through a standard video interface output to a computer for recording and storage of the images. Images are output as a 14-bit data stream for storage in a mass storage device of a computer. The camera may be used to record live IR video, or real-time high speed dynamic events; and is adapted to capture and store thermal images and data at extremely high rates of 50 to 60 Hz up to 900 Hz NTSC/750 Hz PAL.

The IR focal plane array detector is described as a quantum well infrared photodetector and has an image resolution of 320×240 pixels. The 14-bit digital output of the detector permits each pixel of the image array to be assigned an intensity or amplitude value between 1 and 16,383. Thus an individual frame may encompass a broad range of surface temperature and still be able to visualize minute thermal differences. The camera had a spatial resolution (IFOV) of about 1.1 mrad. An excellent description and survey of quantum well IR photodetectors and focal plane arrays has been published as "Quantum Well Infrared Photodetector (QWIP) Focal Plane Arrays by S. D. Gunapala and S. V. Bandara of the Center for Space Microelectronics Technology, Jet Propulsion Laboratory, Pasadena, Calif. in Semiconductors and Semimetals, Vol. 62, 1999.

The image recorder 34 of the exemplary embodiment of the invention is adapted to record or store the images output from the thermal imaging device 18. Image recorder 34 is preferably mass storage in a computer, such as a hard drive, tape drive or similar device. Recorder 34 may also include a video capture card that is adapted to receive and/or buffer the images received as signal output from thermal imaging device 18 prior to storage in mass storage.

Means 38 for integrating the pixel intensity of the exemplary embodiment of the invention is preferably a computer or similar device adapted to access the intensity or amplitude information for each pixel address in each of thermal images 20. Means 38 of the exemplary embodiment of the invention is also adapted to integrate the pixel amplitude or intensity at each pixel address across all or any portion or grouping of thermal images 20. Integration may be performed using well-known numerical integration methods. Means 38 of the exemplary embodiment of the invention is also adapted to incorporate the integrated pixel intensity associated with each address as an element in an array 42 of integrated pixel intensity as a function of pixel address.

Means 38 of the exemplary embodiment of the invention is also adapted to analyze the array 42 of integrated pixel intensity to identify flaws or defects in the object based on variations among the integrated pixel intensity of elements within integrated pixel intensity array 42. Means 38 of the exemplary embodiment of the invention is also preferably adapted to display various representations of integrated pixel intensity array 42, such as by display on a computer monitor. Means 38 of the exemplary embodiment of the invention is also preferably adapted to perform sorting or selection of objects depending on whether flaws or defects are identified in the objects or not. Thus, apparatus 10 may be used in conjunction with the manufacture of objects as an automated inspection system or sorting system.

Figure 2:
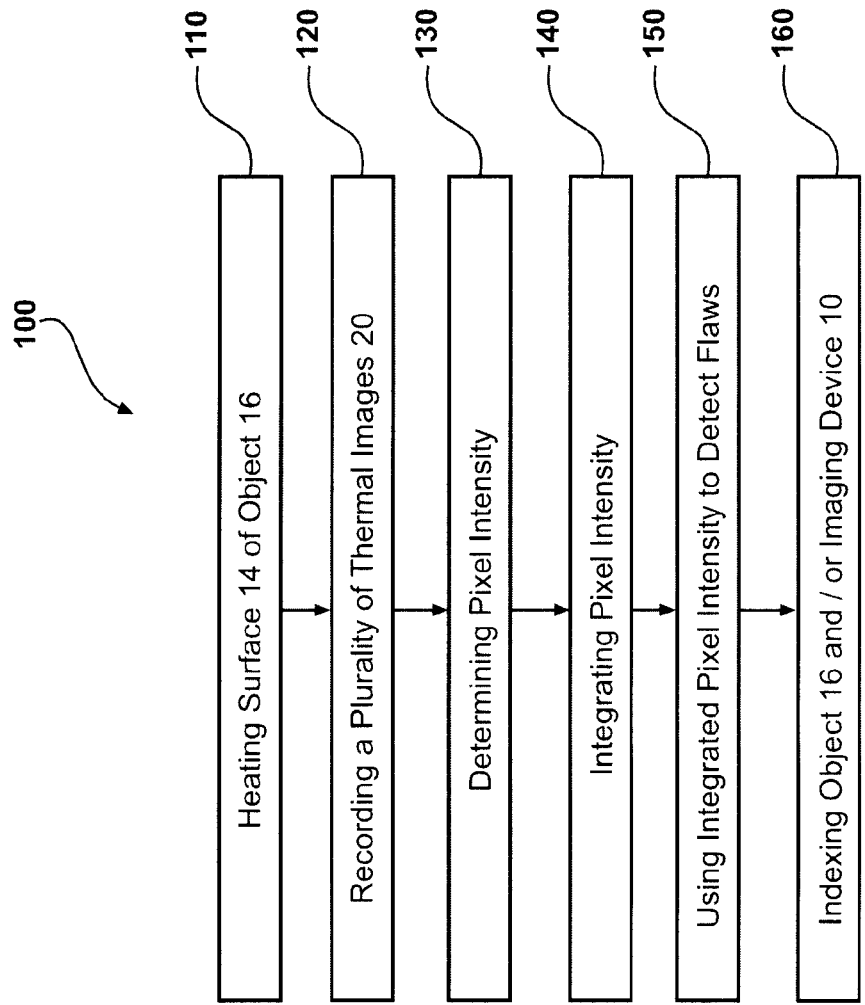
FIG. 2 is a flowchart of the method of the invention.

Referring to FIGS. 1 and 2, in an exemplary method of operation of the present invention, a method 100 includes the step 110 of heating the surface 14 of the object 16 with the heater 12. The surface 14 of object 16 is heated to a sufficient temperature to allow thermographic monitoring. Typically, relatively thin objects only require minimal heating, about 5° C. or less above the ambient object temperature, with as little as about 1° C. or less above ambient object temperature even more preferable. Meanwhile, thicker objects may require significantly greater differential heating, for example, up to about 20° C. above the ambient object temperature has been reported by others using thermographic techniques as desirable for objects having a thickness of about 0.5 inches. Surface factors, including color, emissivity and thermal conductivity, are also important in determining the amount of heat energy to deliver to the surface of the object during heating, while the physical properties establish the upper heating limit at a temperature which will not damage the object 16 and/or surface 14.

In order to accurately locate and determine the size of a flaw, the object surface should be heated to the desired temperature in a sufficiently short period of time so as to inhibit heating of the remainder of the object. However, in order for the apparatus and method of the invention to be effective, the heat applied at the surface must be of a sufficient combination of magnitude, intensity and duration to penetrate to the depth in the object over which it is desirable to detect defects. Therefore, for a given object, relatively lesser amounts of heat energy will be applied to detect surface and near surface defects, and relatively greater amounts of heat energy will be applied to detect defects which are located in regions spaced further away from the surface at which the heat is applied. Typically heating occurs in a fraction of a second for thin objects, but may take substantially longer, perhaps on the order of minutes, for thicker objects. The heating time may also be varied depending on the thermal conductivity of the object, and particularly on the thermal conductivity in the surface region to which the heat is applied.

Figure 3A:
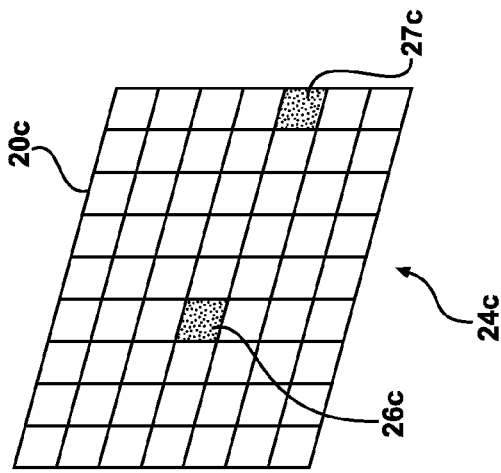
FIG. 3A is a schematic illustration a first thermal image.
Figure 3B:
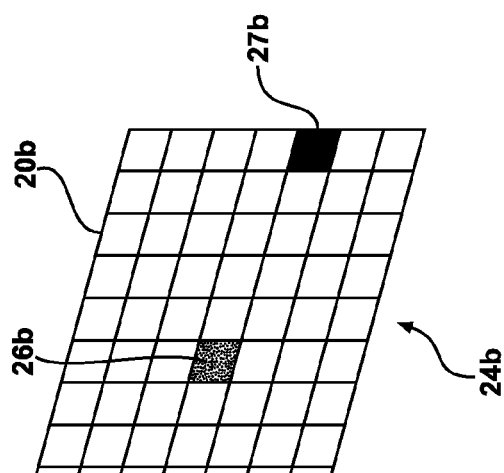
FIG. 3B is a schematic illustration a second thermal image taken after the first thermal image shown in FIG. 3A.
Figure 3C:
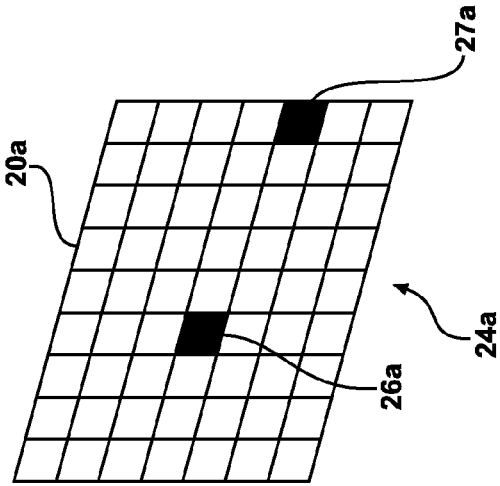
FIG. 3C is a schematic illustration a third thermal image taken after the second thermal image shown in FIG. 3B.

Once the object's surface is heated, the method 100 proceeds with to step 120. At step 120, a plurality of thermal images 20 of the surface 14 are recorded as a function of time using the thermal imaging device 18. Each of the thermal images 20 comprises the array 24 of pixels 26, each pixel 26 having a unique pixel address in the array 24 and corresponding to a surface element in the array of surface elements. FIGS. 3A-3C schematically shows three thermal images 20a, 20b, 20c defining arrays 24a, 24b, 24c. The three thermal images 20a, 20b, 20c correspond to the same portion of the surface and differ in that each of the three thermal images 20a, 20b, 20c is taken at a different time.

Preferably, thermal imaging device 18 is an infrared camera which records and stores successive thermal images 20 of the surface 14 of the object, recording an amplitude or intensity value of each pixel of each image thereof. The number of images recorded depends upon the desired resolution of the resulting integrated array of pixels for that image, the rate at which images are acquired and other factors.

The number of images needed for defect detection is dependent on many variables. The camera's frame rate and the material the part is made from both play a major role in determining the optimal number of images used in the algorithm. Generally, the number of images used to detect defects in low emissivity parts such as metal is less than the number of images used to detect defects in high emissivity parts such as rubber.

At step 130, a pixel intensity or amplitude for each of the pixels 26 in each of the thermal images 20 is determined. The plurality of thermal images 20 are stored in the mass storage of the computer as a corresponding number of arrays 24 of pixels 26, each pixel 26 having an associated pixel intensity. In general, flaws (i.e., a bubble or void) will tend to slow the dissipation of heat from surface 14 of object 16. Therefore, surface elements of the object 16 in which or under which a defect or flaw is located will tend to have higher temperatures than other surface elements. Thus, those pixels 26 of array 24 which are associated with surface elements which include a flaw or defect will tend to register a higher intensity or amplitude than other pixels 26 of array 24.

At step 140, the pixel intensity of pixels 26 having the same address from each of the plurality of thermal images 20 are integrated to establish elements within an array 42 of integrated pixel intensity. This step is partially illustrated in FIG. 3A-3C. Each image 20 is associated with a unique time at which it was recorded. The intensity over time at a particular pixel 26 address may be represented by a polynomial function:

$$f(t) = X_N t^n + X_{N-1} t^{n-1} + X_{N-2} t^{n-2} + \ldots X_{N-n} t^{N-n}$$

The integral of this function may be represented generally by an equation:

$$F(t) = \int_0^N (X_N t^n + X_{N-1} t^{n-1} + X_{n-2} t^{n-2} + \ldots X_{N-n} t^{N-n}) dt$$

This integration is performed for each of the corresponding pixel addresses of the successive images 20.

Figure 3D:
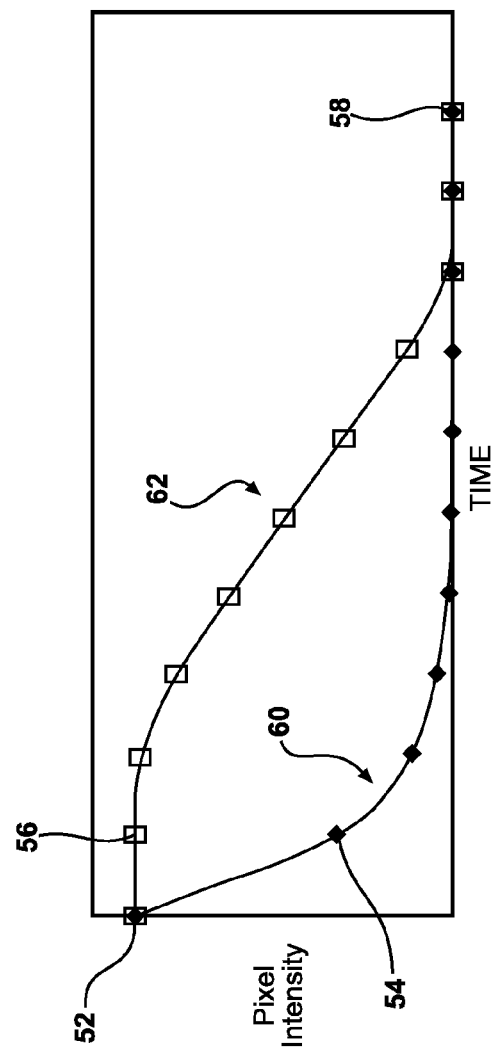
FIG. 3D is a graph of pixel intensity over time corresponding to the pixels shown in FIGS. 3A-3C.

For example, as shown in FIGS. 3A-3D, three pixels 26a, 26b, 26c correspond to the same portion of the surface and differ in that each of the three pixels 26a, 26b, 26c is taken at a different time. Similarly, three pixels 27a, 27b, 27c correspond to the same portion of the surface and differ in that each of the three pixels 27a, 27b, 27c is taken at a different time. FIG. 3D is a graph in which pixel intensity is defined along the y-axis and time is defined along the x-axis. Point 52 of the graph in FIG. 3D corresponds to both of pixels 26a and 27a in FIG. 3A. FIG. 3A shows the pixel intensity of the graph of FIG. 3D reflects this condition. Point 54 of the graph in FIG. 3D corresponds to the pixel 26b in FIG. 3B. Point 56 of the graph in FIG. 3D corresponds to the pixel 27b in FIG. 3B. FIG. 3B shows the pixel 27b is more intense than pixel 26b and the graph of FIG. 3D reflects this condition. Point 58 of the graph in FIG. 3D corresponds to both of pixels 26c and 27c in FIG. 3C. FIG. 3C shows that both of the pixels 26c, 27c are substantially less intense, in comparison with the pixels 26a, 27a in FIG. 3A, and the graph of FIG. 3D reflects this condition.

The intensity time data plotted in FIG. 3D could be utilized in conjunction with well-known regression techniques to determine a polynomial expression which could in turn be integrated. However, to perform a reasonable approximation, the integral may also be obtained by applying numerical integration techniques on the time-based pixel intensity data associated with that pixel address which is obtained from the pixel array 24 information from the recorded images 20. Generally, a curve 60 shown in FIG. 3D is consistent with a portion of the surface without a flaw and a curve 62 is consistent with a portion of the surface with a flaw.

Figure 4:
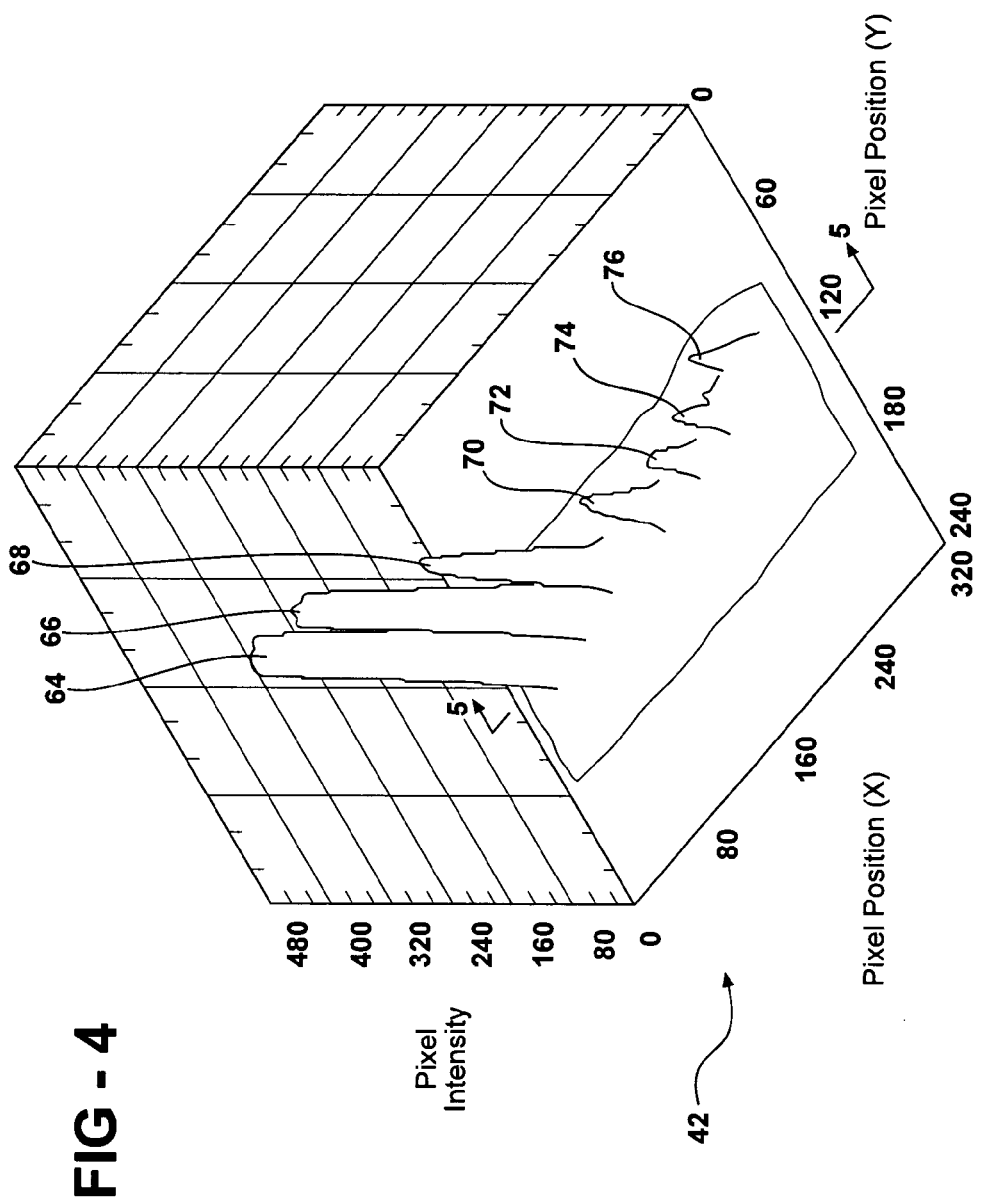
FIG. 4 is a schematic illustration of a plot of integrated pixel intensity as a function of pixel address.

At step 150, the array 42 of integrated pixel intensity is used to detect a flaw in the object 16. Step 150 may be performed in any one of a number of ways. One way of performing step 150 is using the array 42 of integrated pixel intensity to detect a flaw in the object 16. For example, as best shown in FIG. 4, the array 42 provides a three dimensional representation of data. The exemplary array 42 reveals peaks 64, 66, 68, 70, 72, 74, 76 of varying heights from the X-Y plane. The peaks 64, 66, 68, 70, 72, 74, 76 constitute variations of the integrated pixel intensity values between the elements of the array 42 and correspond to flaws in object 16.

Figure 5:
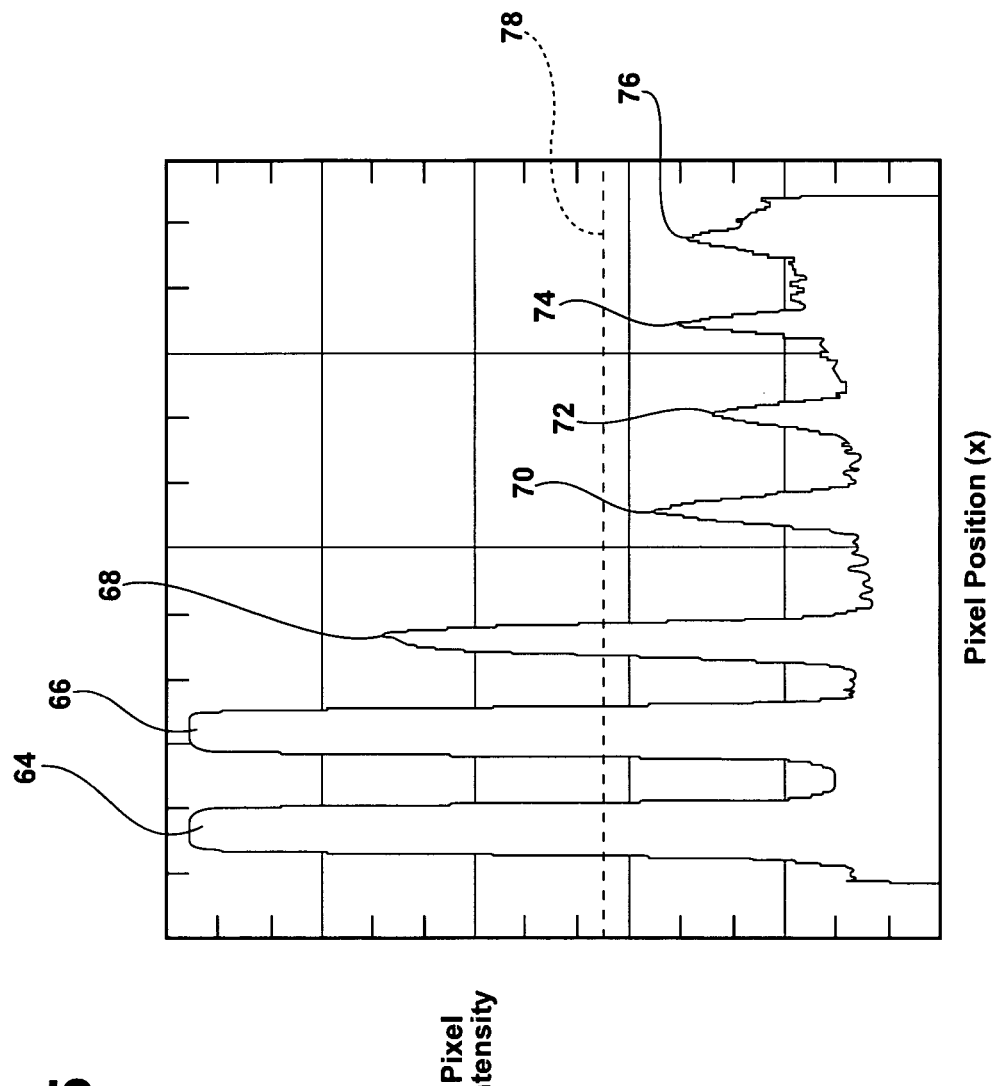
FIG. 5 is a cross-section of the plot of FIG. 4 taken along section line 5-5.

Referring to FIGS. 2 and 5, another method of performing step 150 is by comparing the integrated pixel intensity of individual elements of the array 42 to a predetermined threshold 78. Elements having an integrated pixel intensity greater than the predetermined threshold 78 of pixel intensity are identified as a flaw. In the exemplary array 42, elements corresponding to peaks 64, 66, 68 correspond to a portion of the surface 14 having a flaw. The predetermined threshold 78 of integrated pixel intensity may, for example, be determined empirically from results obtained from samples of the same object 16 made from the same material which are known not to contain defects. The results from such samples may be used to develop a background level of integrated pixel intensity empirically which is representative of samples which do not contain defects. Alternatively, the predetermined threshold 78 value may be a mean value of integrated pixel intensity using standard techniques of calculating the mean, such as by summing all of the values of integrated pixel intensity from one or more images and dividing by the number values summed. Alternately, the predetermined threshold 78 may be a median value of pixel intensity using standard techniques of calculating the median.

The array 42 can be defined by a variety of colors wherein variations in the color reveal flaws in the surface 14. The visual image may be viewed by an operator and defects may be identified using objective criteria, such as predetermined thresholds applied to the display as described above, or subjective criteria such as any number of determinations which may be made by an operator while viewing the display. Similarly, a fourth variation of the integrated pixel intensity among the elements of the array of integrated pixel intensity may also be displayed by creating a visual image of the array in which variations in integrated pixel intensity are correlated to variations in a gray-scale. Still similarly, a fifth alternative method of using variation of the integrated pixel intensity among the elements of the array of integrated pixel intensity is by creating a visual image of the array in which the integrated pixel intensity of an element is plotted as a function of the element address.

It will be appreciated that in order to view all of the surface 14 of an object 16 it may be desirable to index one of the object 16 or the apparatus 10 so as to expose all of the surface 14 to viewing or inspection by the apparatus. As such, the method 100 may also include a step 160 of indexing at least one of the object 16 and the thermal imaging device 10 to expose different portions of the surface 14 to the thermal imaging device 10. It is preferred that the steps of method 100 be executed automatically in response to the execution of a software control algorithm in a computer.

Obviously, many modifications and variations of the present invention are possible in light of the above teachings. It is, therefore, to be understood that within the scope of the appended claims, the invention may be practiced otherwise than as specifically described. The invention is defined by the claims.

What is claimed is:

1. A method for detecting flaws at or substantially immediately below an outer surface of an object of solid material comprising the steps of:

flash heating a portion of the outer surface of the object wherein the outer surface is defined by a plurality of individual surface elements;

recording a plurality of thermal images of the portion over time with a thermal imaging device wherein each of the plurality of thermal images being defined by a plurality of pixels and wherein each of the plurality of pixels having an individual pixel address and corresponding to one of the plurality of individual surface elements;

determining a pixel intensity for each of the plurality pixels in each of the plurality of thermal images;

integrating the pixel intensity of each of the plurality of pixels having the same individual address from respective thermal images to establish elements within an array of integrated pixel intensity, each element representing an integrated pixel intensity for a discrete pixel and integrated pixel intensity location of said discrete pixel in the array; and wherein variations in integrated pixel intensities of various pixel locations are analyzed to identify variations which are indicative of the presence of a flaw; and using the array of said elements of said integrated pixel intensity of said plurality of pixels to detect the flaw in the object to about 0.004 inches below the surface by comparing variations between the integrated pixel intensities of two elements.

2. The method of claim 1 wherein the step of using comprises:

selecting one of the elements in the array to be a representative value for integrated pixel intensity; and comparing the integrated pixel intensity of each of the elements of the array to the representative value of integrated pixel intensity, wherein elements having an integrated pixel intensity greater than the representative value are used to identify a flaw.

3. The method of claim 1 further comprising the step of:

creating a visual image of the array in which variations in integrated pixel intensity are correlated to variations in a color spectrum.

4. The method of claim 1 further comprising the step of:

creating a visual image of the array in which variations in integrated pixel intensity are correlated to variations in a gray-scale.

5. The method of claim 1 further comprising the step of:

creating a visual image of the array in which the integrated pixel intensity of an element is plotted as a function of the element address.

6. The method of claim 1, further comprising the steps of:

indexing at least one of the object and the thermal imaging device to expose different surface portion of the surface to the thermal imaging device; and repeating the steps of claim 1 and said step of indexing for a predetermined number of indexing cycles.

\* \* \* \* \*